US008073240B2

(12) United States Patent
Fischer et al.

(10) Patent No.: US 8,073,240 B2
(45) Date of Patent: Dec. 6, 2011

(54) COMPUTER-IMPLEMENTED METHODS, COMPUTER-READABLE MEDIA, AND SYSTEMS FOR IDENTIFYING ONE OR MORE OPTICAL MODES OF AN INSPECTION SYSTEM AS CANDIDATES FOR USE IN INSPECTION OF A LAYER OF A WAFER

(75) Inventors: Verlyn Fischer, San Jose, CA (US); Chris Maher, Campbell, CA (US); Harish Hiriyannaiah, San Jose, CA (US); Younus Vora, San Jose, CA (US); Ping Ding, San Jose, CA (US); Andrew Hill, San Jose, CA (US)

(73) Assignee: KLA-Tencor Corp., San Jose, CA (US)

( * ) Notice: Subject to any disclaimer, the term of this patent is extended or adjusted under 35 U.S.C. 154(b) by 883 days.

(21) Appl. No.: 12/115,832

(22) Filed: May 6, 2008

(65) Prior Publication Data

US 2008/0279444 A1 Nov. 13, 2008

Related U.S. Application Data

(60) Provisional application No. 60/916,377, filed on May 7, 2007.

(51) Int. Cl.
 *G06K 9/00* (2006.01)
(52) U.S. Cl. .................................................... 382/145
(58) Field of Classification Search ................... None
 See application file for complete search history.

(56) References Cited

U.S. PATENT DOCUMENTS

| 6,487,307 | B1 * | 11/2002 | Hennessey et al. ........... 382/149 |
| 6,674,888 | B1 | 1/2004 | Duzy |
| 7,369,236 | B1 * | 5/2008 | Sali et al. ...................... 356/394 |
| 2005/0052643 | A1 | 3/2005 | Lange et al. |

FOREIGN PATENT DOCUMENTS

WO WO 2007/023502 3/2007

OTHER PUBLICATIONS

International Search Report and Written Opinion for PCT/US08/62870 mailed on Jul. 24, 2008.

\* cited by examiner

*Primary Examiner* — Tu Nguyen
(74) *Attorney, Agent, or Firm* — Ann Marie Mewherter (57) ABSTRACT

Computer-implemented methods, computer-readable media, and systems for identifying one or more optical modes of an inspection system as candidates for use in inspection of a layer of a wafer are provided. One method includes determining one or more characteristics of images of the layer of the wafer acquired using the inspection system and different optical modes available on the inspection system. The method also includes identifying a first portion of the different optical modes as not candidates for use in the inspection of the layer of the wafer based on the one or more characteristics of the images. In addition, the method includes generating output by eliminating the first portion of the different optical modes from the different optical modes at which the images were acquired such that the output includes a second portion of the different optical modes indicated as the candidates for use in the inspection.

19 Claims, 2 Drawing Sheets

COMPUTER-IMPLEMENTED METHODS, COMPUTER-READABLE MEDIA, AND SYSTEMS FOR IDENTIFYING ONE OR MORE OPTICAL MODES OF AN INSPECTION SYSTEM AS CANDIDATES FOR USE IN INSPECTION OF A LAYER OF A WAFER

PRIORITY CLAIM

This application claims priority to U.S. Provisional Application No. 60/916,377 entitled "Computer-Implemented Methods, Carrier Media, and Systems for Identifying One or More Optical Modes of an Inspection System as Candidates for Use in Inspection of a Layer of a Wafer," filed May 7, 2007, which is incorporated by reference as if fully set forth herein.

BACKGROUND OF THE INVENTION

1. Field of the Invention

This invention generally relates to computer-implemented methods, computer-readable media, and systems for identifying one or more optical modes of an inspection system as candidates for use in inspection of a layer of a wafer. Certain embodiments relate to a computer-implemented method for eliminating a first portion of different optical modes available on an inspection system as not candidates for use in inspection based on one or more characteristics of images acquired using the different optical modes.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on a specimen such as a reticle and a wafer. Inspection processes have always been an important part of fabricating semiconductor devices such as integrated circuits. However, as the dimensions of semiconductor devices decrease, inspection processes become even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices. Accordingly, much work in the inspection field has been devoted to designing inspection systems that can detect defects having sizes that were previously negligible.

Inspection for many different types of defects has also become more important recently. For instance, in order to use inspection results to monitor and correct semiconductor fabrication processes, it is often necessary to know what types of defects are present on a wafer. In addition, since controlling every process involved in semiconductor manufacturing is desirable to attain the highest yield possible, it is desirable to have the capability to detect the different types of defects that may result from many different semiconductor processes. The different types of defects that are to be detected may vary dramatically in their characteristics. For example, defects that may be desirable to detect during a semiconductor manufacturing process may include thickness variations, particulate defects, scratches, pattern defects such as missing pattern features or incorrectly sized pattern features, and many others having such disparate characteristics.

Many different types of inspection systems have been developed to detect the different types of defects described above. In addition, most inspection systems are configured to detect multiple different types of defects. In some instances, a system that is configured to detect different types of defects may have adjustable image acquisition and sensitivity parameters such that different parameters can be used to detect different defects or avoid sources of unwanted (nuisance) events. For instance, the spot size, pixel size, or polarization or algorithm settings for angles of collection may be different for an inspection process used to detect particulate defects than for an inspection process used to detect scratches.

Although an inspection system that has adjustable image acquisition and sensitivity parameters presents significant advantages to a semiconductor device manufacturer, these inspection systems are useless if the incorrect image acquisition and sensitivity parameters are used for an inspection process. For example, incorrect or non-optimized image acquisition and sensitivity parameters may produce such high levels of noise that no defects can be detected in the generated inspection data. In addition, since the defects, process conditions, and noise on wafers may vary dramatically (and since the characteristics of the wafers themselves may vary dramatically), the best image acquisition and sensitivity parameters for detecting the defects on a particular wafer may be difficult, if not impossible, to predict. Therefore, although using the correct image acquisition and sensitivity parameters will have a dramatic effect on the results of inspection, it is conceivable that many inspection processes are currently being performed with incorrect or non-optimized image acquisition and sensitivity parameters.

The task of setting up an inspection process for a particular wafer and a particular defect of interest (DOI) may be extremely difficult for a user, particularly when an inspection system has a relatively large number of adjustable image acquisition settings and sensitivity parameters. In addition, it may be impossible to know whether the best inspection process has been found unless all possible combinations of the image acquisition parameters have been tested. However, most inspection processes are currently set up using a large number of manual processes (e.g., manually setting the image acquisition parameters, manually analyzing the resulting inspection data, etc.). As such, setting up the inspection process may take a relatively long time. Furthermore, depending on the types of wafers that will be inspected with the inspection system, a different inspection process may need to be set up for each different type of wafer. Obviously, therefore, setting up the inspection processes for all of the different wafers that are to be inspected may take a prohibitively long time.

Some previously used methods for selecting an optimum optical mode for inspection of a layer of a wafer include inspecting a wafer using a default mode and aggressive detection settings, generating a review sample, and reviewing the wafer using the output of the inspection system (often in the form of a KLA-Tencor review file also commonly referred to as a KLARF) on a scanning electron microscope (SEM) in search of DOI and nuisance events. Such methods may also include classifying the reviewed defects, collecting images of each defect and a reference image using a number of modes where the set of defects for which images are grabbed is a subset of the review sample based on a distribution of class codes. In addition, such methods may include performing signal-to-noise (S/N) analysis on the images collected, inspecting the wafer again at the mode or modes with the most favorable S/N values, generating a new review sample, performing additional SEM review, and optimizing inspection threshold parameters until nuisance defect detection rates are acceptable.

Such methods, however, have a number of disadvantages. For example, in such methods, identifying DOI is required in order to evaluate a mode. However, it is possible and likely that the default mode will not detect the DOI. Discovery that DOI was not detected happens well into the process at the SEM review step. When this occurs, the user must go back to the start of the process and choose another mode with which to scan. Failing to detect DOI using the default mode, therefore, results in wasted time and can be substantially severe if the DOI is continually not detected by the mode(s) used for scanning the wafer.

Another disadvantage is that even if DOI are detected at the first step of the process, the collection of images for a reasonable sample of DOI and nuisance events at every inspection mode is impossible due to time constraints. Without images at a particular mode, the methods described above are not able to evaluate that mode. Since unevaluated modes are no longer candidates for mode selection, there is a risk that valuable modes have been discarded. Even when only a subset of modes are evaluated, the time required is substantially long.

An additional disadvantage is that the methods described above rely on the existence and identification of DOI and the evaluation of each mode using these DOI. However, there are cases in which a user would like to choose an optimal mode or modes using a setup wafer that does not have DOI or without identifying DOI on a wafer regardless of whether DOI are located thereon. The only recourse in the methods described above is to use the default mode which has a relatively high risk of not being an optimal mode.

Accordingly, it would be advantageous to develop computer-implemented methods, computer-readable media, and/or systems for identifying one or more optical modes of an inspection system as candidates for use in inspection of a layer of a wafer that are less labor intensive, quicker, and less tedious than previously used methods and that result in optical modes selected for inspection of a layer on a wafer that are more appropriate, or even optimal, for the inspection than optical modes selected using the methods described above.

SUMMARY OF THE INVENTION

The following description of various embodiments of computer-implemented methods, computer-readable media, and systems is not to be construed in any way as limiting the subject matter of the appended claims.

One embodiment relates to a computer-implemented method for identifying one or more optical modes of an inspection system as candidates for use in inspection of a layer of a wafer. The method includes determining one or more characteristics of images of the layer of the wafer acquired using the inspection system and different optical modes available on the inspection system. The method also includes identifying a first portion of the different optical modes as not candidates for use in the inspection of the layer of the wafer based on the one or more characteristics of the images. In addition, the method includes generating output by eliminating the first portion of the different optical modes from the different optical modes at which the images were acquired such that the output includes a second portion of the different optical modes indicated as the candidates for use in the inspection of the layer of the wafer.

In one embodiment, the images are acquired in a region of interest on the layer of the wafer. In another embodiment, the method includes selecting the different optical modes used to acquire the images based on a type of the inspection that will be performed on the layer of the wafer. In an additional embodiment, the different optical modes used to acquire the images include all of the optical modes available on the inspection system. In a further embodiment, the method includes identifying one or more optical modes of the inspection system prior to acquiring the images of the layer of the wafer that are not candidates for use in the inspection of the layer of the wafer based on optics theory, empirical evidence, or some combination thereof. In one such embodiment, acquiring the images does not include acquiring the images at the one or more identified optical modes.

In one embodiment, the one or more characteristics of the images include spatial contrast, material contrast, pattern suppression, saturation, or some combination thereof. In another embodiment, the identifying step includes identifying the different optical modes included in the first portion as the different optical modes used to acquire the images that do not have the best values for the one or more characteristics. In an additional embodiment, the identifying step includes identifying the images for which the best value of each of the one or more characteristics is determined and identifying the first portion as the different optical modes that were not used to acquire the identified images. In a further embodiment, the second portion of the different optical modes includes each of the different optical modes used to acquire the images having the best value for each of the one or more characteristics.

In one embodiment, the method includes automatically acquiring additional images of the layer of the wafer using the second portion of the different optical modes, determining one or more additional characteristics of the additional images, and comparing the one or more additional characteristics of the additional images to determine which of the second portion of the different optical modes is the best candidate for use in the inspection of the layer. In one such embodiment, the one or more additional characteristics of the additional images include signal-to-noise (S/N) of defects in the additional images. In another embodiment, the method includes determining S/N in additional images acquired using the second portion of the different optical modes and selecting one of the second portion of the different optical modes as the best candidate for use in the inspection of the layer based on the S/N.

In one embodiment, the different optical modes are defined by different values for one or more first parameters of the inspection system and values that are the same for one or more second parameters of the inspection system. In one such embodiment, the one or more first parameters include wavelength, aperture, pixel size, or some combination thereof. In another such embodiment, the output also includes the second portion of the different optical modes with different values for the one or more second parameters of the inspection system. In an additional such embodiment, the one or more second parameters include focus offset, inspection speed, polarization settings or some combination thereof.

In one embodiment, all steps of the method are performed without knowledge of defects of interest (DOI) on the layer of the wafer. In another embodiment, all steps of the method are performed without identifying DOT on the layer of the wafer.

Each of the steps of each of the embodiments of the method described above may be further performed as described herein. In addition, each of the embodiments of the method described above may include any other step(s) of any other method(s) described herein. Furthermore, each of the embodiments of the method described above may be performed by any of the systems described herein.

Another embodiment relates to a computer-readable medium that includes program instructions executable on a computer system for performing a computer-implemented method for identifying one or more optical modes of an inspection system as candidates for use in inspection of a layer of a wafer. The computer-implemented method includes determining one or more characteristics of images of the layer of the wafer acquired using the inspection system and different optical modes available on the inspection system. The method also includes identifying a first portion of the different optical modes as not candidates for use in the inspection of the layer of the wafer based on the one or more characteristics of the images. In addition, the method includes generating output by eliminating the first portion of the different optical modes from the different optical modes at which the images were acquired such that the output includes a second portion of the different optical modes indicated as the candidates for use in the inspection of the layer of the wafer.

The computer-readable medium described above may be further configured as described herein. The steps of the computer-implemented method may be further performed as described herein. In addition, the computer-implemented method for which the program instructions are executable may include any other step(s) of any other method(s) described herein.

An additional embodiment relates to a system configured to identify one or more optical modes of an inspection system as candidates for use in inspection of a layer of a wafer. The system includes an inspection system configured to acquire images of the layer of the wafer using different optical modes available on the inspection system. The system also includes a computer system configured to determine one or more characteristics of the images. The computer system is also configured to identify a first portion of the different optical modes as not candidates for use in the inspection of the layer of the wafer based on the one or more characteristics of the images. In addition, the computer system is configured to generate output by eliminating the first portion of the different optical modes from the different optical modes at which the images were acquired such that the output includes a second portion of the different optical modes indicated as the candidates for use in the inspection of the layer of the wafer. The system may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities. One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the embodiments may be used for identifying one or more optical modes of an inspection system as candidates for use in inspection of another specimen such as a reticle, which may also be commonly referred to as a mask or a photomask. Many different types of reticles are known in the art, and the terms "reticle," "mask," and "photomask" as used herein are intended to encompass all types of reticles known in the art.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
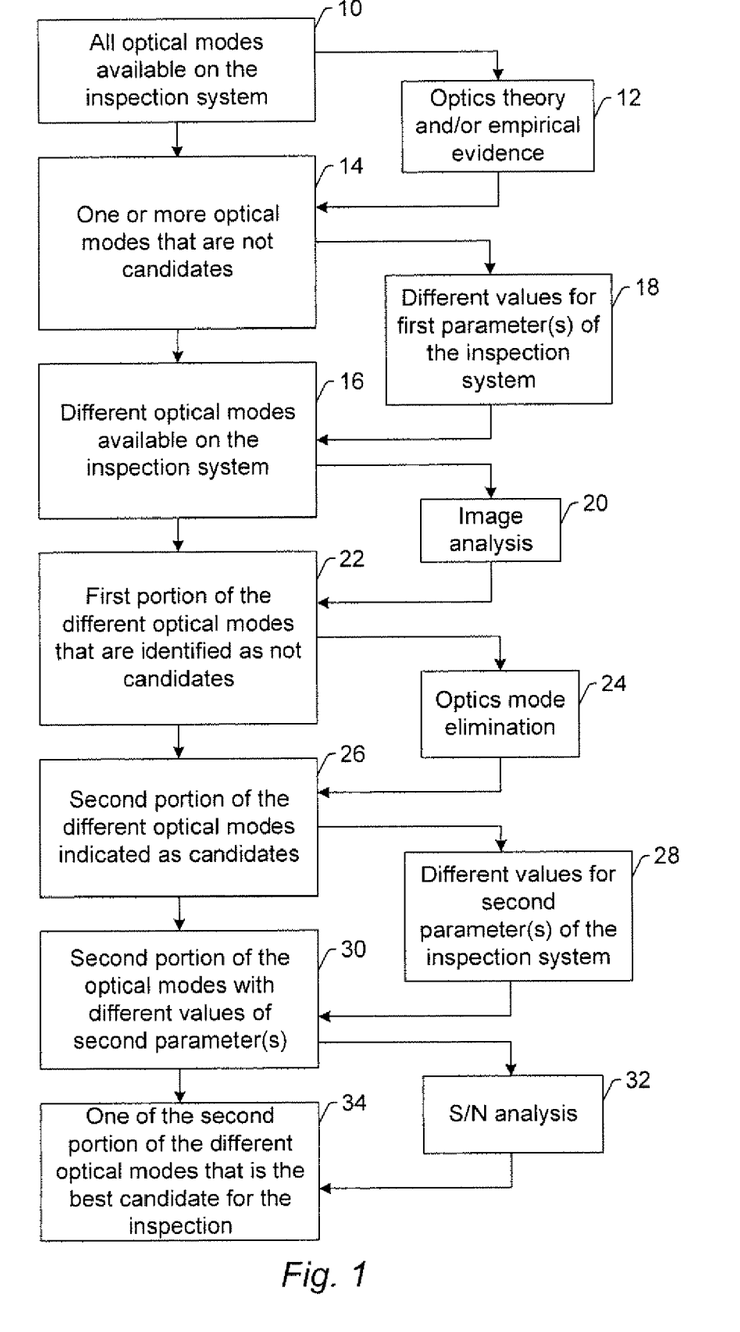
FIG. 1 is a flow chart illustrating one embodiment of a computer-implemented method for identifying one or more optical modes of an inspection system as candidates for use in inspection of a layer of a wafer.

One embodiment relates to a computer-implemented method for identifying one or more optical modes of an inspection system as candidates for use in inspection of a layer of a wafer. One embodiment of such a computer-implemented method is shown in FIG. 1. It is noted that all of the steps shown in FIG. 1 are not essential to practice of the method. One or more steps may be omitted or added to the method illustrated in FIG. 1, and the method can still be practiced within the scope of these embodiments.

In one embodiment, the inspection system includes a dark field (DF) inspection system. The DF inspection system may be configured as described further herein. In other embodiments, the inspection system includes a bright field (BF)

inspection system. The BF inspection system may have any suitable configuration known in the art. The inspection system may also be configured for inspection of patterned wafers and/or unpatterned wafers.

The embodiments described herein can be used to assist a user in selecting the optimum combination of optics for inspecting a layer of a wafer for defects. The desired effect of the embodiments described herein will be to reduce the time involved in choosing one or more appropriate combinations of optics without unacceptable risk of eliminating a valuable combination in the process. For example, a single optical combination, typically referred to as a "mode," includes a number of optical components including, but not limited to, a wavelength filter, an aperture, and an objective set. Since the number of modes increases like the product of the number of components available the total number of modes can be substantially high. However, the embodiments described herein can significantly reduce the number of modes that must be evaluated to identify the optimum optical mode without eliminating a valuable combination in the process. In particular, the embodiments described herein may be used to perform a wafer inspection system optical modes selection reduction methodology to eliminate certain modes from further consideration. Therefore, the embodiments described herein can improve ease of use for the inspection system by significantly reducing the set up time. With the optimal setup, the signal-to-noise ratio (S/N) for a given process layer can be considerably enhanced, and thus the inspection sensitivity can be greatly improved.

As described above, the embodiments may be used to assist a user in selection of an optical mode for inspection of a layer on a wafer. For example, the embodiments described herein may be implemented as a "software wizard" in the recipe set up portion of software on an inspection system. The software wizard may include any type of software that can be configured to perform one or more steps of the methods described herein. The user may initiate the software wizard, and the wizard may guide the user through a series of steps. In this manner, the embodiments described herein may be configured to assist the user in making certain decisions for one or more steps of the embodiments. In addition, the embodiments described herein may be configured to perform one or more steps based on input from a user. However, in some embodiments, all steps of the method are performed without user intervention. For example, all steps of the methods described herein may be performed automatically. Therefore, the methods described herein may be fully automated processes.

The method includes determining one or more characteristics of images of the layer of the wafer acquired using the inspection system and different optical modes available on the inspection system. The embodiments described herein may include acquiring the images of the layer of the wafer using the inspection system and different optical modes available on the inspection system. For example, the software wizard described above may be configured to automatically orchestrate image collection. However, the embodiments described herein may or may not include acquiring the images by imaging the wafer. For example, the embodiments described herein may include acquiring the images from an inspection system that generated the images or from a storage medium (e.g., a storage medium of the inspection system, a fab database, etc.) in which the inspection system stored the images. In any case, the images may be acquired in any suitable manner (e.g., by scanning a layer of the wafer using the different optical modes of the inspection system).

In one embodiment, the images are acquired in a region of interest on the layer of the wafer. The region of interest may be selected by a user. For example, the user may indicate portions of a die on the wafer that are regions of interest, and the inspection system may collect images of those regions as dictated by the elimination methodology and/or subsequent analysis of images. The regions of interest may be defined in periodic and random regions of the die. The user may be guided through this step by the software wizard described above. In addition, the software may be configured such that the user can select the region or regions of interest in any suitable manner (e.g., by drawing one or more boxes around the region or regions of interest in an image of a die displayed to the user). Furthermore, the user may or may not have information about the care areas on the wafer prior to selecting the region or regions of interest. Therefore, the region or regions of interest may or may not correspond to the care areas. In addition, even if the user has information about the care areas on the wafer prior to selecting the region or regions of interest, the region or regions of interest may not be the same as the care areas on the wafer. For instance, the region or regions of interest may be smaller than the care areas.

In one embodiment, the different optical modes used to acquire the images include all of the optical modes available on the inspection system. In this manner, the starting point for the embodiments described herein may include all of the optical modes available on the inspection system. For example, as shown in block 10 of FIG. 1, the starting point may include all optical modes available on the inspection system. In this manner, each of the available optical modes may be evaluated as described further herein thereby ensuring that the best possible optical mode is not missed by not being evaluated. However, since the number of available optical modes on the inspection system may number well into the tens or hundreds, the embodiments described herein can eliminate some of the available optical modes as described herein before starting the evaluation of the optical modes.

In another embodiment, the method includes selecting the different optical modes used to acquire the images based on a type of the inspection that will be performed on the layer of the wafer. For example, a user may perform wafer alignment and wafer layout set up steps and create a base test indicating either "array," "random," or "mixed" type inspection. "Mixed" type inspection may be inspection for both array and random areas on the wafer. In addition, the user may select a region of interest on the wafer as described above, and the embodiments described herein may be configured to determine the type of area or areas included in the region of interest. For example, the embodiments described herein may include determining one or more characteristics of the region of interest such as periodicity or pitch of patterns in the region of interest using a technique such as pattern recognition or image analysis. In this manner, the embodiments described herein may include determining the type of inspection that will be performed on the layer of the wafer. At this stage, the test need not include light level learn locations and need not include care area regions. In one such example, if the user indicates that the type of inspection is array, the different optical modes used to acquire the images may be selected to include modes at a given pixel size that is known to be appropriate or optimal for array inspection with different combinations of wavelengths and apertures. In this manner, the type of inspection that will be performed on the layer of the wafer may determine the starting point for the embodiments described herein (e.g., the starting point for the image acquisition and/or analysis described herein).

In a further embodiment, the method includes identifying one or more optical modes of the inspection system prior to acquiring the images of the layer of the wafer that are not candidates for use in the inspection of the layer of the wafer based on optics theory, empirical evidence, or some combination thereof. In one such embodiment, acquiring the images does not include acquiring the images at the one or more identified optical modes. For example, as shown in FIG. 1, optics theory and/or empirical evidence 12 may be used to evaluate all optical modes available on the inspection system shown in block 10 to identify one or more optical modes that are not candidates, as shown in block 14. The one or more optical modes that are not candidates shown in block 14 may then be removed from all optical modes available on the inspection system shown in block 10 and therefore may not be further considered by evaluation performed as described herein.

In this manner, the method may perform an elimination methodology that is based on a combination of optics theory and some empirical evidence resulting from experience (e.g., many years of experience) with wafer inspection technology. For example, based on optics theory and information about the patterns formed on the wafer (e.g., information about the pitch of the patterns), the apertures that will suppress such patterns at least to some degree in images acquired by the inspection system can be determined. Therefore, the optical modes used to acquire the images and that are evaluated as described herein may include only those optical modes that include apertures that will suppress the patterns to at least some degree. In another example, based on empirical evidence and information about the layer on the wafer (e.g., whether the layer is a contact layer, a layer that does not include metal grains, etc.), the wavelengths that are more appropriate for the layer on the wafer may be determined. In this manner, the optical modes used to acquire the images and that are evaluated as described herein may include only those modes that include wavelengths that are at least somewhat appropriate for the layer on the wafer that will be inspected. As such, the elimination methodology that may be performed by the embodiments described herein addresses the problem of mode selection from a theoretical point of view instead of the "brute force" methods used in the past.

In one embodiment, the different optical modes are defined by different values for one or more first parameters of the inspection system and values that are the same for one or more second parameters of the inspection system. In one such embodiment, the one or more first parameters include wavelength, aperture, pixel size, or some combination thereof. In this manner, the method may include down selecting or eliminating one or more optical modes based on a first set of parameters of the inspection system. For example, as described above, the method may include identifying one or more optical modes that are not candidates shown in block 14 of FIG. 1 and removing these optical mode(s) from all optical modes available on the inspection system. In some such embodiments, different optical modes available on the inspection system shown in block 16 at which the images are acquired are defined by different values for first parameter(s) of the inspection system shown in block 18. The different values for the first parameter(s) may be a predetermined set of different values (e.g., all of the different values available on the inspection system for the first parameter(s)). Alternatively, the different values for the first parameter(s) may be selected as described herein (e.g., based on the type of inspection that will be performed on the layer of the wafer).

Furthermore, as shown in FIG. 1, the different optical modes available on the inspection system shown in block 16 at which images are acquired may be generated by modifying one or more parameters of the available optical modes shown in block 10 that are remaining after the one or more optical modes that are not candidates shown in block 14 have been eliminated. However, all optical modes available on the inspection system shown in block 10 may include modes with different values for the one or more first parameters. Therefore, the modes remaining after the one or more optical modes that are not candidates have been eliminated may not be modified as described above since they may already be defined by different values for first parameter(s) of the inspection system.

In one embodiment, the one or more characteristics of the images include spatial contrast, material contrast, pattern suppression, saturation, or some combination thereof. Such characteristic(s) of the images may be determined using any suitable image analysis techniques known in the art. Spatial contrast may be generally defined as a measure of the spatial resolution of the image. The spatial contrast may be determined based on the total contrast of the image. In addition, if two or more materials are imaged in a single image, the two or more materials may have different contrasts in the image. In this manner, the spatial contrast may be determined based on the different contrasts of the different materials. Furthermore, the contrasts of fewer than all of the materials may be used to determine the spatial contrast of the images. Material contrast may be generally defined as a measure of the contrast between different materials in the image. Therefore, the material contrast is a measure of image contrast. The pattern suppression may be a measure of how well a pattern formed on the wafer was suppressed in the images. Saturation of the images refers to contrast saturation of the images.

The characteristics of the images that are determined as described herein may vary depending on, for example, the type of inspection that will be performed on the layer of the wafer, which may be selected by the user as described herein. For example, for array type inspections, the one or more characteristics determined for the images may include, but are not limited to, pattern suppression and gray level suppression. In another example, for random type inspection, other image characteristics (or "metrics") may be determined such as, but not limited to, contrast, spatial resolution, noise metrics, etc.

The method also includes identifying a first portion of the different optical modes as not candidates for use in the inspection of the layer of the wafer based on the one or more characteristics of the images. For example, as shown in FIG. 1, images acquired by the different optical modes available on the inspection system shown in block 16 may be evaluated by image analysis 20, which may be performed as described herein, to determine the first portion of the different optical modes that are identified as not candidates shown in block 22. Therefore, the embodiments described herein may include the application of image analysis techniques (such as analyses of spatial contrast, material contrast, pattern suppression, saturation, or some combination thereof) in conjunction with the elimination methodology described further herein. For example, as the images are analyzed, modes may be eliminated from further consideration (e.g., from analysis performed in one or more steps described further herein) according to the elimination methodology.

In another embodiment, the identifying step includes identifying the different optical modes included in the first portion as the different optical modes used to acquire the images that do not have the best values for the one or more characteristics. For example, one of the characteristics that is determined for the images may include pattern suppression. Therefore, the pattern suppression in the images acquired using different modes may be compared, and the modes that produced images that do not have the best pattern suppression may be identified for inclusion in the first portion of the different optical modes that are eliminated from further consideration as described herein. In another example, one of the characteristics that is determined for the images may include gray level suppression. In this example, the gray level suppression in the images acquired using different modes may be compared, and the modes that produced images that do not have the best gray level suppression may be identified for inclusion in the first portion of the different modes that are eliminated from further consideration as described herein.

In an additional embodiment, the identifying step includes identifying the images for which the best value of each of the one or more characteristics is determined and identifying the first portion as the different optical modes that were not used to acquire the identified images. For example, if the one or more characteristics that are determined for the images include pattern suppression and gray level suppression, the images having the best pattern suppression or the best gray level suppression may be identified, and the optical modes that were not used to acquire these images may be identified for inclusion in the first portion of the different optical modes and may be eliminated as described further herein.

In a further embodiment, the second portion of the different optical modes includes each of the different optical modes used to acquire the images having the best value for each of the one or more characteristics. For example, when considering more than one characteristic, different modes may have the best values for different characteristics. In this manner, one mode may not have the best values for all of the different characteristics. Therefore, the modes that are identified for inclusion in the first portion may include those modes that do not have the best values for any of the different characteristics. By process of elimination, therefore, based on the examples of the characteristics described above, the different optical modes included in the second portion, which are not eliminated prior to further consideration as described herein, may include one optical mode used to acquire the images having the best value for pattern suppression, another optical mode used to acquire the images having the best value for gray level suppression, etc. In this manner, the number of the different optical modes that are not included in the first portion and therefore are not eliminated from further consideration may be equal to the number of characteristics of the images determined and used in the embodiments described herein. In addition, the number of the different optical modes that are not included in the first portion and therefore are not eliminated from further consideration may be less than the number of characteristics of the images determined and used in the embodiments described herein if one mode was used to acquire images having the best values for more than one characteristic.

As described above, the characteristic(s) of the images that are determined in the embodiments described herein may vary depending on, for example, the type of inspection that will be performed on the wafer. Therefore, the characteristic(s) of the images that are used in the embodiments described herein to identify the first portion of the different optical modes may also vary depending on the type of inspection that will be performed on the wafer. For example, for array type inspection, the characteristic(s) of the images used to identify the first portion of the different optical modes may include pattern suppression and gray level suppression. Therefore, the best values of these characteristics may include the best pattern suppression and the best gray level suppression. In another example, for random type inspection, the characteristic(s) of the images used to identify the first portion of the optical modes may include contrast, spatial resolution, noise metrics, etc. Therefore, the best values of these characteristics may include the maximum contrast, the best spatial resolution, the best (lowest) noise metrics, etc.

The method further includes generating output by eliminating the first portion of the different optical modes from the different optical modes at which the images were acquired such that the output includes a second portion of the different optical modes indicated as the candidates for use in the inspection of the layer of the wafer. For example, as shown in FIG. 1, the first portion of the different optical modes that are identified as not candidates shown in block 22 may be eliminated from the different optical modes available on the inspection system shown in block 16 by optics mode elimination 24 to produce the second portion of the different optical modes indicated as candidates shown in block 26. Therefore, the embodiments described herein may be configured to perform an optics component evaluation methodology that also functions as an elimination methodology. In addition, the number of modes that can be evaluated and eliminated using this methodology is significant. For example, an inspection system can be configured to have about 50 to about 250 different calibrated optical modes depending on the particular system configuration. The embodiments described herein can be used to evaluate all of the calibrated optical modes available on any inspection system, and a substantial number of these calibrated optical modes (e.g., more than 90%) can be eliminated from further consideration thereby making selection of an optimal optical mode substantially faster (e.g., since most optical modes have already been eliminated).

The output may include any suitable output (e.g., a list, a table, etc.) that can be used to indicate the second portion of the different optical modes as candidates for use in the inspection of the layer of the wafer. In addition, the method may include providing the output to a user. The output may be provided to a user in any suitable manner such as by displaying the output to a user. For example, after the elimination methodology has run its course thereby eliminating the first portion of the different optical modes, the user may be presented with recommendations for each mode. In another example, the software wizard described above may automatically orchestrate the image analysis described above and when complete may provide the user with results based on the to modes investigated. It is likely that most modes will be marked as "eliminate from further consideration" with a few being marked as "use this mode to find defects of interest (DOI)" and/or "only use this mode for S/N analysis." In this manner, the recommendations that are presented to the user may essentially be suggestions for which modes to evaluate or try first. In addition, the wizard session may be saved (e.g., in any of the storage media described herein) such that users can retrieve the information at the same point in the recipe setup or at a later point during S/N analysis, which may be performed as described further herein.

As described above, in one embodiment, the different optical modes are defined by different values for one or more first parameters of the inspection system and values that are the same for one or more second parameters of the inspection system. In one such embodiment, the one or more first parameters include wavelength, aperture, pixel size, or some combination thereof. In this manner, the method may include down selecting or eliminating one or more optical modes based on a first set of parameters of the inspection system. After down selecting the one or more optical modes based on the first set of parameters, the method may include down selecting other parameters of the inspection system by varying one or more of the other parameters of the inspection system for each of the optical modes that were not eliminated to thereby generate the second portion of the different optical modes that will be evaluated to determine the best optical mode for inspection of the layer of the wafer. For example, as shown in FIG. 1, the second portion of the different optical modes indicated as candidates shown in block 26 may be modified using different values for second parameter(s) of the inspection system shown in block 28 to produce the second portion of the optical modes with different values of the second parameter(s) shown in block 30. In this manner, in some embodiments, the output also includes the second portion of the different optical modes with different values for the second parameter(s) of the inspection system. In an additional such embodiment, the one or more second parameters include focus offset, inspection speed, polarization settings (e.g., polarization settings for illumination and/or collection), or some combination thereof. The different values for the second parameter(s) may be a predetermined set of different values (e.g., all of the different values available on the inspection system for the second parameter(s)). Alternatively, the different values for the second parameter(s) may be selected as described herein (e.g., based on the type of inspection that will be performed on the layer of the wafer).

In one such example, if 4 characteristics of the images are used to identify the first portion of the optical modes that are eliminated, the second portion of the optical modes may include 4 optical modes. One or more additional parameters of the 4 optical modes may be varied to arrive at perhaps 20 optical modes that are evaluated as described further herein.

In one embodiment, the method includes automatically acquiring additional images of the layer of the wafer using the second portion of the different optical modes, determining one or more additional characteristics of the additional images, and comparing the one or more additional characteristics of the additional images to determine which of the second portion of the different optical modes is the best candidate for use in the inspection of the layer. The additional images may be acquired as described herein. In one such embodiment, the one or more additional characteristics of the additional images include S/N of defects in the additional images. In another embodiment, the method includes determining S/N in additional images acquired using the second portion of the different optical modes and selecting one of the second portion of the different optical modes as the best candidate for use in the inspection of the layer based on the S/N. For example, as shown in FIG. 1, the second portion of the optical modes with different values of the second parameter(s) shown in block 30 may be evaluated using S/N analysis 32 to determine one of the second portion of the different optical modes that is the best candidate for the inspection shown in block 34.

In this manner, the method may be configured for the integration of automated image collection capabilities and S/N analysis techniques, which can be used after the elimination methodology described above for final mode selection. The set of modes for which S/N will be evaluated as described herein is significantly reduced and will include only those that were not marked as "eliminate from further consideration" or with another similar indicia. The S/N analysis techniques may include any suitable S/N analysis techniques. In addition, the method may include presenting the user with the outcome of the elimination methodology before, during, or after the S/N analysis. With this information, the user or the methods described herein can determine and make improved decisions about whether to investigate additional modes or not.

In one example, after the first portion of the different optical modes has been eliminated as described above, the user may perform a number of steps including any of those described further herein. For example, the user or the method may replace a default mode with one of the "use this mode to find DOI" modes for inspection of a layer of a wafer with relatively aggressive detection settings (e.g., to perform "hot scans" of the wafer). Scanning the wafer using the revised default mode may be performed on the same region or regions of interest for which the images used to eliminate some of the optical modes were acquired. The user or the method may generate a review sample. The review sample may be generated automatically by the embodiments described herein. The review sample may also be generated in any suitable manner known in the art. The user or the method may then review the defects using the output of the inspection system (which may often be in the form of a KLA-Tencor review file, which may also be referred to as a KLARF) using a review system such as a scanning electron microscope (SEM) in search of DOI and nuisance events. The user or the method may classify the reviewed defects. The method may classify the reviewed defects using any suitable classification technique(s). In this manner, DOI such as repeater defects may be separated from nuisance defects, and the DOI may be sampled to evaluate the second portion of the different optical modes, which may be performed as described further herein.

In one such example, if there are 20 optical modes that are to be evaluated by S/N analysis, which may be defined as described above, images of DOI may be grabbed using each of the 20 modes, and the S/N for each of the images of the DOI may be determined. The S/N values may be compared, and 1 or 2 of the 20 optical modes that were used to acquire the images having the highest S/N values may be selected as the best optical modes. These top 1 or 2 optical modes (and any of the results described herein such as the S/N values or images of various DOI) may be presented to a user in any suitable manner. The user may then select one, some, all, or none of the optical modes for use in the inspection of the layer of the wafer.

In some such embodiments, the method may include inspecting the wafer again at the mode or modes with the most favorable S/N values. Such inspection may alternatively be performed by the user. In addition, such inspection may be performed as described further herein. The method may also include generating a new review sample. Alternatively, the user may generate the new review sample. The new review sample may be generated in any suitable manner known in the art. In addition, the method may include performing additional review (e.g., SEM review) using the new review sample. The additional review may alternatively be performed by the user. The additional review may be performed in any suitable manner.

The method may further include optimizing inspection threshold parameters until nuisance defect rates are acceptable. Alternatively, optimization of the inspection threshold parameters may be performed by a user. The inspection threshold parameters may be optimized in any suitable manner. In addition, the method may include selecting one or more parameters of a defect detection algorithm that will be used to detect defects on the wafer based on the images acquired using the inspection system and the optical mode selected for use in the inspection. The defect detection algorithm may include any suitable defect detection algorithm known in the art. The one or more parameters of the defect detection algorithm that are selected may include the threshold and/or any other parameters of the defect detection algorithm. The one or more parameters of the defect detection algorithm may be selected in any suitable manner.

In an additional embodiment, all steps of the method are performed without knowledge of DOI on the layer of the wafer. In a further embodiment, all steps of the method are performed without identifying DOI on the layer of the wafer. In other words, the steps may be performed as described further herein regardless of whether or not DOI on the layer of the wafer have been identified.

In contrast, in previously used methods, a user may perform a quick scan of the wafer, then review some of the defects detected using results of the quick scan. The user may then use the results of the review to identify at least some DOI on the layer. An additional scan or additional scans may then be performed at different optical modes to grab images of the identified DOI. The images may then be processed to determine the intensity of the defects in the images versus the intensity of the background in the images to measure the S/N of the defects detected using different optical modes. The images of DOI are used in this method to ensure that the optical mode, which is selected based on the images and the S/N determined using the images, is appropriate for detecting DOI on the layer of the wafer. Otherwise, optical modes that increase the detection of nuisance defects may be inadvertently selected for use for inspection of the layer of the wafer, which is disadvantageous for obvious reasons.

In order to perform such methods, therefore, the user must not only identify DOI using the results of the review, which may take a substantially long time particularly if the quick scan is performed with an optical mode that results in substantial nuisance detection or noise or that reduces the detection of DOI, but also must have some knowledge about the DOI, which may not always be available to the user. For example, if the user selects defects for which images are to be grabbed that are not DOI, the optical mode that is selected based on measurements performed on such images may be suboptimal for detecting the true DOI. In contrast, since the embodiments described herein can be performed without knowledge of the DOI, the embodiments described herein can be used to determine the optical mode for the inspection of the layer of the wafer quicker than previously used methods and regardless of whether knowledge about the DOI is available. In addition, the optical mode that is selected using the embodiments described herein may more likely be optimal for detecting DOI than an optical mode selected using previously used methods even though knowledge of the DOI may not be used in the embodiments described herein.

In one embodiment, the method is performed for different layers on the wafer. For example, the method may be performed separately for different layers on the wafer. In this manner, different optical modes may be selected to be used for inspection of different layers on the wafer. The different layers on the wafer may be inspected using the same inspection system. In this manner, different optical modes may be used with the same inspection system for inspection of different layers of the wafer. In addition, the different layers on the wafer may be inspected using different inspection systems. For example, the methods described herein may be performed for any inspection system based on knowledge about the different optical modes that are available on the inspection system. In this manner, the optical mode for inspection of each different layer on the wafer may be optimized using the embodiments described herein. As such, the optical mode for inspection of each different layer on the wafer may be optimized thereby optimizing the S/N and sensitivity of inspection for each different layer using the embodiments described herein.

Each of the embodiments of the method described above may include any other step(s) of any other method(s) described herein. Furthermore, each of the embodiments of the method described above may be performed by any of the systems described herein.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method selects one of the optical modes as the best candidate, the method may include storing the selected optical mode in an inspection recipe in a storage medium. Furthermore, the results may be stored "permanently," "semi-permanently," temporarily, or for some period of time. For example, the storage medium may be random access memory (RAM), and the results may not necessarily persist indefinitely in the storage medium.

The embodiments described herein have a number of advantages over other methods and systems for selecting one or more parameters of an inspection system for inspection of a layer of a wafer. For example, the embodiments described herein drastically reduce the time in which an optical mode can be determined compared to the previously used methods. In particular, the embodiments described herein reduce the inspection and review iterations necessary to find a DOI and reduce the number of images that are collected. In addition, the embodiments significantly increase the odds that a user will determine the best mode using the embodiments described herein even if the user has not identified a DOI. Therefore, users can achieve better inspection system performance in a shorter period of time using the embodiments described herein.

Many different users can also benefit from the embodiments described herein. For example, "expert" users of the inspection system whose goal is to build an optimum inspection recipe over a period of a few days can benefit greatly from the embodiments described herein. In addition, a reduction in the time that it takes to select an optimum optical mode will leave more time to optimize other recipe parameters (e.g., focus offset, inspection speed, defect detection algorithm parameters, etc.) thereby resulting in better overall results. In another example, users of the inspection system in production type environments whose goal is to build quality production recipes may benefit greatly from the embodiments described herein. In particular, poor recipe quality can cost customers millions of dollars in lost revenue if critical defect types are missed during production. However, often such production users are forced to build sub-optimal inspection recipes due to time constraints, and the embodiments described herein would allow such users to build better inspection recipes in a similar amount of time.

Figure 2:
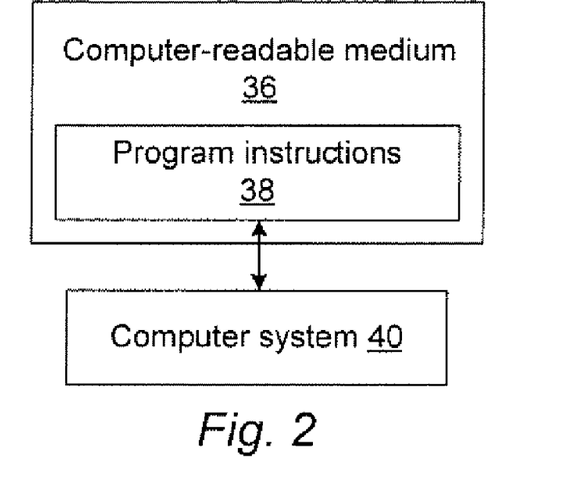
FIG. 2 is a block diagram illustrating one embodiment of a computer-readable medium that includes program instructions executable on a computer system for performing one or more of the computer-implemented methods described herein.

An additional embodiment relates to a computer-readable medium that includes program instructions executable on a computer system for performing a computer-implemented method for identifying one or more optical modes of an inspection system as candidates for use in inspection of a layer of a wafer. One such embodiment is shown in FIG. 2. In particular, as shown in FIG. 2, computer-readable medium 36 includes program instructions 38 executable on computer system 40.

The computer-implemented method includes determining one or more characteristics of images of the layer of the wafer acquired using the inspection system and different optical modes available on the inspection system. Determining the one or more characteristics of the images may be performed as described herein. The method also includes identifying a first portion of the different optical modes as not candidates for use in the inspection of the layer of the wafer based on the one or more characteristics of the images. Identifying the first portion of the different optical modes may be performed as described herein. In addition, the method includes generating output by eliminating the first portion of the different optical modes from the different optical modes at which the images were acquired such that the output includes a second portion of the different optical modes indicated as the candidates for use in the inspection of the layer of the wafer. Generating the output may be performed as described further herein. The computer-implemented method for which the program instructions are executable may include any other step(s) described herein.

Program instructions 38 implementing methods such as those described herein may be transmitted over or stored on computer-readable medium 36. The computer-readable medium may be a transmission medium such as a wire, cable, or wireless transmission link. The computer-readable medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 3:
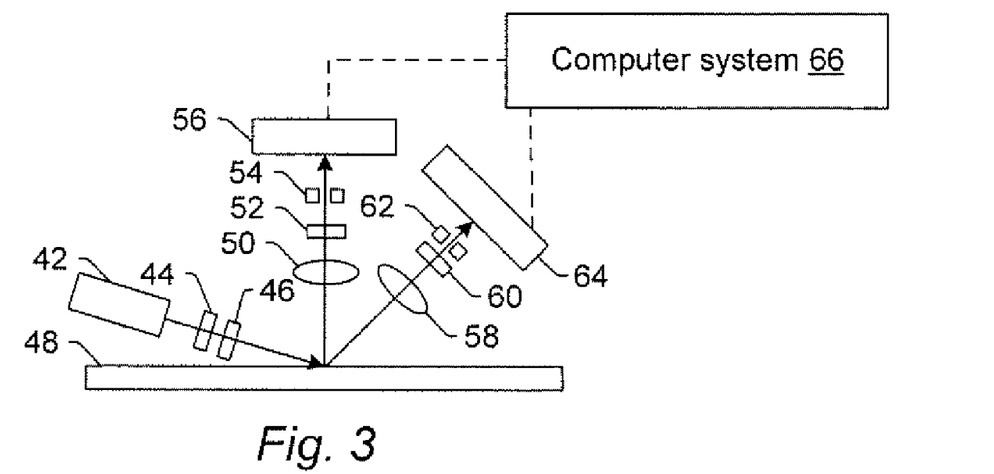
FIG. 3 is a schematic diagram illustrating a side view of a system configured to identify one or more optical modes of an inspection system as candidates for use in inspection of a layer of a wafer.

Another embodiment relates to a system configured to identify one or more optical modes of an inspection system as candidates for use in inspection of a layer of a wafer. One embodiment of such a system is shown in FIG. 3. The system includes an inspection system configured to acquire images of the layer of the wafer using different optical modes available on the inspection system. For example, as shown in FIG. 3, the inspection system includes light source 42. Light source 42 may include any suitable light source known in the art such as a laser.

Light source 42 is configured to direct light to filter 44, which may be a spectral filter or any other suitable filter that can be used to alter or select the wavelength(s) of the light from light source 42 that is or are used for inspection and/or acquiring the images described herein. In addition, the inspection system may include more than one filter (not shown), each of which may be positioned independently in the path of the light from the light source. Each of the filters may be configured to alter the wavelength(s) of the light from the light source in a different manner. The inspection system may be configured to move the filters into and out of the path of the light from the light source in any suitable manner depending on which wavelength(s) of light is or are selected for illumination of the wafer during acquisition of the images or inspection. The filter that is positioned in the path of the light from the light source during acquisition of the images or inspection may be selected as described herein.

Light from filter 44 may be directed to polarizing component 46, which may include any suitable polarizing component known in the art. In addition, the inspection system may include more than one polarizing component (not shown), each of which may be positioned independently in the path of the light from the filter. Each of the polarizing components may be configured to alter the polarization of the light from the filter in a different manner. The inspection system may be configured to move the polarizing components into and out of the path of the light from the filter in any suitable manner depending on which polarization setting is selected for illumination of the wafer during acquisition of the images or inspection. The polarization setting used for the illumination of the wafer during acquisition of the images or inspection may be selected as described herein and may include any appropriate polarization setting (e.g., p-polarized (P), s-polarized (S), and circularly polarized (C)). In addition, although the light from light source 42 is shown in FIG. 3 to pass through filter 44 and then polarizing component 46, it is to be understood that the light from the light source may pass through polarizing component 46 before passing through filter 44. In other words, the positions of the filter and the polarizing component in the path of the light from the light source shown in FIG. 3 may be reversed.

Light exiting polarizing component 46 is directed to wafer 48 at an oblique angle of incidence, which may include any suitable oblique angle of incidence. The inspection system may also include one or more optical components (not shown) that are configured to direct light from light source 42 to filter 44, from filter 44 to polarizing component 46, or from polarizing component 46 to wafer 48. The optical components may include any suitable optical components known in the art such as, but not limited to, a reflective optical component. In addition, the light source, the filter, the polarizing component, and optionally the one or more optical components may be configured to direct the light to the wafer at one or more angles of incidence (e.g., an oblique angle of incidence and/or a substantially normal angle of incidence). The inspection system may be configured to acquire the images described herein by scanning the light over the wafer in any suitable manner.

Light scattered from wafer 48 may be collected and detected by multiple channels of the inspection system during acquisition of the images and during inspection. For example, light scattered from wafer 48 at angles relatively close to normal may be collected by lens 50. Lens 50 may include a refractive optical element as shown in FIG. 3. In addition, lens 50 may include one or more refractive optical elements and/or one or more reflective optical elements. Light collected by lens 50 may be directed to polarizing component 52, which may include any suitable polarizing component known in the art. In addition, the inspection system may include more than one polarizing component (not shown), each of which may be positioned independently in the path of the light collected by the lens. Each of the polarizing components may be configured to alter the polarization of the light collected by the lens in a different manner. The inspection system may be configured to move the polarizing components into and out of the path of the light collected by the lens in any suitable manner depending on which polarization setting is selected for detection of the light collected by lens 50 during acquisition of the images or inspection. The polarization setting used for the detection of the light collected by lens 50 during acquisition of the images or inspection may be selected as described herein and may include any suitable polarization setting (e.g., P, S, and non-polarized (N)).

Light exiting polarizing component 52 may be directed to aperture 54, which may include any suitable aperture known in the art. In addition, the inspection system may include more than one aperture (not shown), each of which may be positioned independently in the path of the light collected by the lens or exiting polarizing component 52. Each of the apertures may be configured to block a portion of the light exiting the polarizing component or the light collected by the lens in a different manner. The inspection system may be configured to move the apertures into and out of the path of the light exiting the polarizing component or the light collected by the lens in any suitable manner depending on which aperture is selected for acquisition of the images or inspection. The aperture that is positioned in the path of the light exiting polarizing component 52 or the light collected by lens 50 during acquisition of the images or inspection may be selected as described herein. In addition, although the light collected by lens 50 is shown to pass through polarizing component 52 and then aperture 54, it is to be understood that the light collected by the lens may pass through aperture 54 before passing through polarizing component 52. In other words, the positions of the polarizing component and the aperture in the path of the light collected by lens 50 shown in FIG. 3 may be reversed.

Light exiting aperture 54 is directed to detector 56. Detector 56 may include any suitable detector known in the art such as a charge coupled device (CCD) or another type of imaging detector. Detector 56 is configured to generate output that is responsive to the scattered light collected by lens 50 and transmitted by polarizing component 52 and aperture 54 if positioned in the path of the collected scattered light. Therefore, lens 50, polarizing component 52 if positioned in the path of the light collected by lens 50, aperture 54 if positioned in the path of the light exiting polarizing component 52, and detector 56 form one channel of the inspection system. This channel of the inspection system may include any other suitable optical components (not shown) known in the art such as a spectral filter.

Light scattered from wafer 48 at different angles may be collected by lens 58. Lens 58 may be configured as described above. Light collected by lens 58 may be directed to polarizing component 60, which may include any suitable polarizing component known in the art. In addition, the inspection system may include more than one polarizing component (not shown), each of which may be positioned independently in the path of the light collected by the lens. Each of the polarizing components may be configured to alter the polarization of the light collected by the lens in a different manner. The inspection system may be configured to move the polarizing components into and out of the path of the light collected by the lens in any suitable manner depending on which polarization setting is selected for detection of the light collected by lens 58 during acquisition of the images or inspection. The polarization setting used for detection of the light collected by lens 58 during acquisition of the images or inspection may be selected as described herein and may include any suitable polarization setting (e.g., P, S, and N).

Light exiting polarizing component 60 may be directed to aperture 62, which may include any suitable aperture known in the art. In addition, the inspection system may include more than one aperture (not shown), each of which may be positioned independently in the path of the light collected by lens 58 or exiting polarizing component 60. Each of the apertures may be configured to block a portion of the light exiting the polarizing component or the light collected by the lens in a different manner. The inspection system may be configured to move the apertures into and out of the path of the light exiting the polarizing component or the light collected by the lens in any suitable manner depending on which aperture is selected for acquisition of the images or inspection. The aperture that is positioned in the path of the light exiting polarizing component 60 or the light collected by lens 58 during acquisition of the images or inspection may be selected as described herein. In addition, although the light collected by lens 58 is shown in FIG. 3 to pass through polarizing component 60 and then aperture 62, it is to be understood that the light collected by the lens may pass through aperture 62 before passing through polarizing component 60. In other words, the positions of the polarizing component and the aperture in the path of the light collected by lens 58 shown in FIG. 3 may be reversed.

Light exiting aperture 62 is directed to detector 64, which may be configured as described above. Detector 64 is configured to generate output that is responsive to the collected scattered light that passes through aperture 62 if positioned in the path of the scattered light. Therefore, lens 58, polarizing component 60 if positioned in the path of the light collected by lens 58, aperture 62 if positioned in the path of the light exiting polarizing component 60, and detector 64 may form another channel of the inspection system. This channel may also include any other optical components (not shown) described above. In some embodiments, lens 58 may be configured to collect light scattered from the wafer at polar angles from about 20 degrees to about 70 degrees. In addition, lens 58 may be configured as a reflective optical component (not shown) that is configured to collect light scattered from the wafer at azimuthal angles of about 360 degrees.

The inspection system shown in FIG. 3 may also include one or more other channels (not shown). For example, the inspection system may include an additional channel, which may include any of the optical components described herein such as a lens, one or more polarizing components, one or more apertures, and a detector, configured as a side channel. The lens, the one or more polarizing components, the one or more apertures, and the detector may be further configured as described herein. In one such example, the side channel may be configured to collect and detect light that is scattered out of the plane of incidence (e.g., the side channel may include a lens that is centered in a plane that is substantially perpendicular to the plane of incidence and a detector configured to detect light collected by the lens).

The system also includes computer system 66. Output generated by the detectors during acquisition of the images and during inspection may be provided to computer system 66. For example, the computer system may be coupled to each of the detectors (e.g., by one or more transmission media shown by the dotted lines in FIG. 3, which may include any suitable transmission media known in the art) such that the computer system may receive the output generated by the detectors. The computer system may be coupled to each of the detectors in any other suitable manner.

The computer system is configured to determine one or more characteristics of the images. The computer system may be configured to determine the one or more characteristics of the images as described further herein. The computer system is also configured to identify a first portion of the different optical modes as not candidates for use in the inspection of the layer of the wafer based on the one or more characteristics of the images. The computer system may be configured to identify the first portion of the different optical modes as described further herein. In addition, the computer system is configured to generate output by eliminating the first portion of the different optical modes from the different optical modes at which the images were acquired such that the output includes a second portion of the different optical modes indicated as the candidates for use in the inspection of the layer of the wafer. The computer system may be configured to generate the output as described further herein.

The computer system may be configured to perform any other step(s) of any method embodiment(s) described herein. The computer system may be further configured as described herein. The inspection system may also be further configured as described herein. Furthermore, the system may be further configured as described herein.

It is noted that FIG. 3 is provided herein to generally illustrate one configuration of an inspection system that may be included in the system embodiments described herein. Obviously, the inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system) such as the Puma 9000 and 9100 series of tools that are commercially available from KLA-Tencor, San Jose, Calif. For some such systems, the methods described herein may be provided as optional functionality of the system (e.g., in addition to other functionality of the system). Alternatively, the system described herein may be designed "from scratch" to provide a completely new system.

In some embodiments, a system configured to perform one or more of the computer-implemented methods described herein may include an inspection system such as that described above. However, a system that is configured to perform one or more of the computer-implemented methods described herein may not include an inspection system. For example, the system may include one or more processors or one or more computer systems configured as a stand alone tool. In one such example, the system may include one or more components that are specifically designed (and optionally dedicated) to performing one or more of the computer-implemented methods described herein.

Further modifications and alternative embodiments of various aspects of the invention may be apparent to those skilled in the art in view of this description. For example, computer-implemented methods, computer-readable media, and systems for identifying one or more optical modes of an inspection system as candidates for use in inspection of a layer of a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for identifying one or more optical modes of an inspection system as candidates for use in inspection of a layer of a wafer, comprising:

determining one or more characteristics of images of the layer of the wafer acquired using the inspection system and different optical modes available on the inspection system;

identifying a first portion of the different optical modes as not candidates for use in the inspection of the layer of the wafer based on the one or more characteristics of the images; and generating output by eliminating the first portion of the different optical modes from the different optical modes at which the images were acquired such that the output comprises a second portion of the different optical modes indicated as the candidates for use in the inspection of the layer of the wafer, wherein all steps of the method are performed without identifying defects of interest on the layer of the wafer.

2. The method of claim 1, wherein the images are acquired in a region of interest on the layer of the wafer.

3. The method of claim 1, further comprising selecting the different optical modes used to acquire the images based on a type of the inspection that will be performed on the layer of the wafer.

4. The method of claim 1, wherein the different optical modes used to acquire the images comprise all of the optical modes available on the inspection system.

5. The method of claim 1, further comprising identifying one or more optical modes of the inspection system prior to acquiring the images of the layer of the wafer that are not candidates for use in the inspection of the layer of the wafer based on optics theory, empirical evidence, or some combination thereof, wherein said acquiring does not comprise acquiring the images at the one or more identified optical modes.

6. The method of claim 1, wherein the one or more characteristics of the images comprise spatial contrast, material contrast, pattern suppression, saturation, or some combination thereof.

7. The method of claim 1, wherein said identifying comprises identifying the different optical modes included in the first portion as the different optical modes used to acquire the images that do not have the best values for the one or more characteristics.

8. The method of claim 1, wherein said identifying comprises identifying the images for which the best value of each of the one or more characteristics is determined and identifying the first portion as the different optical modes that were not used to acquire the identified images.

9. The method of claim 1, wherein the second portion of the different optical modes comprises each of the different optical modes used to acquire the images having the best value for each of the one or more characteristics, 10. The method of claim 1, further comprising automatically acquiring additional images of the layer of the wafer using the second portion of the different optical modes, determining one or more additional characteristics of the additional images, and comparing the one or more additional characteristics of the additional images to determine which of the second portion of the different optical modes is the best candidate for use in the inspection of the layer.

11. The method of claim 10, wherein the one or more additional characteristics of the additional images comprise signal-to-noise of defects in the additional images.

12. The method of claim 1, further comprising determining signal-to-noise in additional images acquired using the second portion of the different optical modes and selecting one of the second portion of the different optical modes as the best candidate for use in the inspection of the layer based on the signal-to-noise.

13. The method of claim 1, wherein the different optical modes are defined by different values for one or more first parameters of the inspection system and values that are the same for one or more second parameters of the inspection system.

14. The method of claim 13, wherein the one or more first parameters comprise wavelength, aperture, pixel size, or some combination thereof.

15. The method of claim 13, wherein the output further comprises the second portion of the different optical modes with different values for the one or more second parameters of the inspection system.

16. The method of claim 13, wherein the one or more second parameters comprise focus offset, inspection speed, polarization settings, or some combination thereof.

17. The method of claim 1, wherein all steps of the method are further performed without knowledge of the defects of interest on the layer of the wafer.

18. A non-transitory computer-readable medium, comprising program instructions executable on a computer system for performing a computer-implemented method for identifying one or more optical modes of an inspection system as candidates for use in inspection of a layer of a wafer, wherein the computer-implemented method comprises:
   determining one or more characteristics of images of the layer of the wafer acquired using the inspection system and different optical modes available on the inspection system;
   identifying a first portion of the different optical modes as not candidates for use in the inspection of the layer of the wafer based on the one or more characteristics of the images; and
   generating output by eliminating the first portion of the different optical modes from the different optical modes at which the images were acquired such that the output comprises a second portion of the different optical modes indicated as the candidates for use in the inspection of the layer of the wafer, wherein all steps of the method are performed without identifying defects of interest on the layer of the wafer.

19. A system configured to identify one or more optical modes of an inspection system as candidates for use in inspection of a layer of a wafer, comprising:
   an inspection system configured to acquire images of the layer of the wafer using different optical modes available on the inspection system; and
   a computer system configured to:
      determine one or more characteristics of the images;
      identify a first portion of the different optical modes as not candidates for use in the inspection of the layer of the wafer based on the one or more characteristics of the images; and
      generate output by eliminating the first portion of the different optical modes from the different optical modes at which the images were acquired such that the output comprises a second portion of the different optical modes indicated as the candidates for use in the inspection of the layer of the wafer, wherein the computer system is further configured to determine the one or more characteristics, identify the first portion, and generate the output without identifying defects of interest on the layer of the wafer.

* * * * *